United States Patent [19]
Elion et al.

[11] 3,956,277
[45] May 11, 1976

[54] PURINE SUGAR DERIVATIVES

[75] Inventors: Gertrude B. Elion, Chapel Hill;
Janet E. Litster, Raleigh; Lowrie M. Beacham, III, Durham, all of N.C.

[73] Assignee: Burroughs Wellcome Co., Research Triangle Park, N.C.

[22] Filed: Nov. 15, 1971

[21] Appl. No.: 198,991

[30] Foreign Application Priority Data
Nov. 16, 1970 United Kingdom............... 54504/70

[52] U.S. Cl............................ 260/211.5 R; 424/180
[51] Int. Cl.² ................... C07H 19/16; C07H 19/18
[58] Field of Search ............................ 260/211.5 R

[56] References Cited
UNITED STATES PATENTS

| | | | |
|---|---|---|---|
| 3,074,929 | 1/1963 | Hitchings et al. | 260/211.5 R |
| 3,074,930 | 1/1963 | Hitchings et al. | 260/211.5 R |
| 3,167,540 | 1/1965 | Pike et al. | 260/211.5 R |
| 3,180,859 | 4/1965 | Hoeksema | 260/211.5 R |
| 3,208,997 | 9/1965 | Iwai et al. | 260/211.5 R |
| 3,225,029 | 12/1965 | Yamaoka | 260/211.5 R |
| 3,269,917 | 8/1966 | Imada et al. | 260/211.5 R |
| 3,328,388 | 6/1967 | Shen et al. | 260/211.5 R |
| 3,404,144 | 10/1968 | Fox et al. | 260/211.5 R |
| 3,463,850 | 8/1969 | Shen et al. | 260/211.5 R |
| 3,595,853 | 7/1971 | Kanai et al. | 260/211.5 R |

*Primary Examiner*—Johnnie R. Brown
*Attorney, Agent, or Firm*—Donald Brown

[57] ABSTRACT

This invention relates to purine sugar derivatives which are useful as suppressors of the immune response and as antiviral agents, and to methods of preparation thereof.

5 Claims, No Drawings

PURINE SUGAR DERIVATIVES

According to the present invention there is provided a compound of formula (I) or a pharmaceutically acceptable salt thereof,

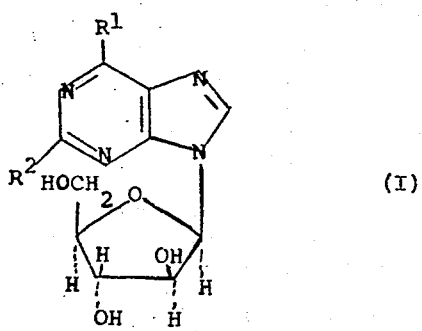

wherein $R^1$ is a mercapto or lower alkylthio group and $R^2$ is an amino group or a hydrogen atom, or $R^1$ is an amino group and $R^2$ is a hydroxy group, provided that whenever $R^1$ is a mercapto or methylthio group, $R^2$ is an amino group. These compounds have a β-configuration regarding the linkage between the purine and the D-arabinofuranosyl moiety. In particular, a compound of formula (I) wherein $R^2$ is an amino group is preferred.

As used herein and throughout the specification the term "lower" alkyl is denoted to mean 1 to 4 carbon atoms, preferably 1 to 3 carbon atoms and most preferably 1 to 2 carbon atoms.

Salts which are especially preferred for therapeutic use are salts of pharmaceutically acceptable carboxylic acids such as lactic, acetic, malic as well as salts of pharmaceutically acceptable mineral acids, such as hydrochloric or sulphuric acid. The activity of any salt administered or used medically resides in the base. In addition to the above, toxic salts can be made and converted into either the base or pharmaceutically acceptable salts by standard methods, e.g. a metathetical reaction.

The compounds of formula (I) are particularly useful in treating viral infections resulting from DNA viruses, such as vaccinia and herpes. Additional uses of these compounds are in suppressing the immune response of an animal or a human patient to the transplant of foreign cells into the body and in the treatment of autoimmune diseases in mammals such as lupus erythematosus, haemolytic anaemia, ulcerative colitis and nephrosis.

In another aspect there is provided a pharmaceutical composition or preparation, comprising a compound of formula (I') or a pharmaceutically acceptable salt thereof,

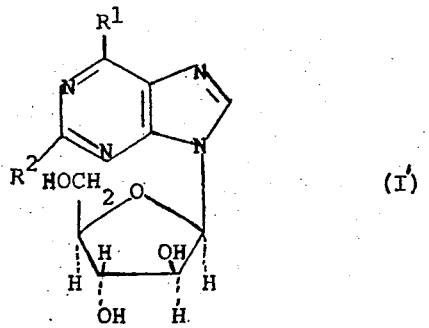

wherein $R^1$ is a mercapto or lower alkylthio group and $R^2$ is an amino group or a hydrogen atom, or one of $R^1$ and $R^2$ is a hydroxy group and the other is an amino group, in association with a pharmaceutically acceptable carrier therefor or in an effective unit dosage form. In a particular aspect the above composition comprises a compound of formula (I), as hereinbefore defined. Preferably the compound of Formula (I') has the substituent $R^2$ as an amino group.

As used herein the term "effective unit dosage" is denoted to mean a predetermined antiviral amount sufficient to be effective against the organism in vivo. Pharmaceutically acceptable carriers are materials recommended for the purpose of administering the medicament, and may be liquid, solid or gaseous materials, which are otherwise inert or medically acceptable and are compatible with the active ingredients. Aqueous solutions of 6-methylthio and 2-amino-6-hydroxy-9-(β-D-arabinofuranosyl)purines, other than in a sterile form presented in a sealed container, are not within the scope of the invention in this respect.

These pharmaceutical compositions may be given parenterally, orally, used as a suppository, applied as an optic solution, or applied topically as an ointment, cream, powder, etc, depending on whether the preparation is used to treat internal or external viral infections or is used as an immune or autoimmune response suppressant.

For internal viral infections the compositions are used orally or parenterally at dose levels, calculated on the base, of about 5 to 250 mg/kg, preferably 20 to 100 mg/kg, of mammal bodyweight, and is preferably used in man in a unit dosage form, administered a few times daily in the amount of 10 mg/unit dose.

For use as immune suppressants, the compositions are administered internally a few times daily at dosages preferably of about 3 to 10 mg/kg of mammal bodyweight.

For oral administration, fine powders or granules may contain diluting, dispersing and/or surface active agents, and may be presented in a draught, in water or in syrup, in capsules or sachets in the dry state or in a non-aqueous suspension, wherein suspending agents may be included, in tablets, when binders and lubricants may be included, or in a suspension in water or a syrup. Where desirable or necessary flavouring, preserving, suspending, thickening or emulsifying agents can be included. Tablets and granules are preferred, and these may be coated.

For parenteral administration, the compounds may be presented in aqueous injection solutions in a concentration of about 0.1 to 10%, preferably 1% w/v which may contain antioxidants, buffers etc.

For viral infections of the eye or other external tissues the compositions are preferably applied to the infected part of the body of the patient as a topical ointment, at a dosage of about one half of that used for internal use, i.e. up to 125 mg/kg or 5 to 125 mg per unit dose.

Of the compounds of formula (I'), the comopunds 2-amino-6-hydroxy and especially 2-amino-6-mercapto-9-(β-D-arabinofuranosyl)purines are the most preferred, particularly for their extremely high antiviral activity as, for example, against the herpes virus. Substantial and unexpectedly high activity against vaccinia virus has also been shown and they have been found to be unexpectedly useful in suppressing the immune response to transplanted cells.

According to the present invention a compound of formula (I), as hereinbefore defined, may conveniently be prepared according to a first method, by reducing a compound of formula (II),

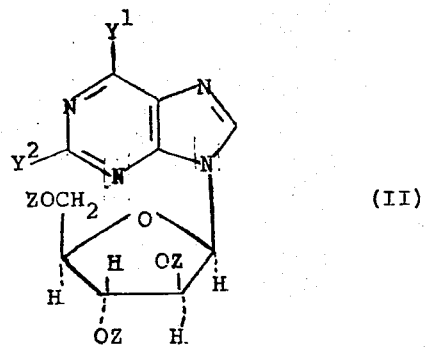

wherein $Y^1$ is a protected mercapto group or an amino group and $Y^2$ is an amino group or a hydrogen atom, provided that when $Y^1$ is an amino group, $Y^2$ is an amino group, and Z is a hydroxyl-blocking group, and a. alkylating any resulting 6-mercapto-9-($\beta$-D-arabinofuranosyl) purine with an alkyl group having at least two carbon atoms to form the 6-alkylthio substituted compound; or b. converting any resulting 2,6-diamino-9-($\beta$-D-arabinofuranosyl) purine into the 2-hydroxy-6-amino substituted compound by diazotisation and hydrolysis; or c. optionally alkylating any resulting 2-amino-6-mercapto-9-($\beta$-D-arabinofuranosyl)purine to form the 2-amino-6-alkylthio substituted compound.

The mercapto- protecting group may be a lower alkyl group, preferably a methyl group, or a substituted or unsubstituted arylalkyl group such as a benzyl group e.g. a p-phenylbenzyl, α- or β- menaphthyl (naphth-1(or 2-)-yl-methyl) group.

Z must be such that a. when attached to the oxygen atom at position two of the sugar moiety, there is no interference with processes at C(1) of the sugar b. it is removable, when, desired, under mild conditions.

Thus Z may be a substituted or unsubstituted arylalkyl group as listed above, and preferably a benzyl group.

The reduction may be accomplished by either chemical or catalytic methods. Thus catalytic methods employing Raney nickel, palladium, palladised charcoal or platinum black in a hydrogen atomsphere, generally at superatmospheric pressures, may be used. Chemical reduction with reducing agents of the type producing hydrogen atoms in situ, such as alkali metal, preferably sodium, in liquid ammonia, is especially useful.

Alkylation according to either of steps (a) and (c) may readily be effected by reaction with an alkyl halide, for example methyl iodide, in dimethylsulphoxide in the presence of anhydrous potassium carbonate. In step (b) the 2,6-diamino substituted purine is partially diazotised with nitrous acid, for example by mixing a solution of sodium nitrite with hydrochloric acid, and the product is hydrolysed with water.

2-Amino-6-hydroxy-9-($\beta$-D-arabinofuranosyl)purine, falling within the scope of compounds of formula (I'), may be prepared according to the process described by Reist in *Biochemistry* 1964, 3, 15–18 or alternatively by enzymatically deaminating selectively the 2,6-diamino compound at the 6-position with adenosine deaminase. The preparation of 6-methylthio-9-($\beta$-D-arabinofuranosyl)purine may follow the general process described for compounds of formula (I) including the alkylation step (a).

The compounds of formula (I) may also be prepared according to a second method, from the anomeric xylosides via the lyxosides following the general procedures described by Reist et al. in *J. Org. Chem.*, 1962, 27, 3274 and *Biochemistry* Ibid., wherein the final stage in the formation of the arabinoside ring is the ring-opening of the corresponding 2,3-anhydro-$\beta$-D-lyxofuranosyl derivative by treatment with a base suitable for hydrolysis, such as sodium acetate, in an inert solvent such as aqueous dimethylformamide.

Whenever the end substitution in the 2 or 6 position in the purine ring is required to be a hydrogen atom or an amino group, the xyloside starting material conveniently already carries this substituent in the desired position. When hydroxy, mercapto or alkylthio substitution is required, the starting material advantageously carries a halogen atom, such as a chlorine atom, in the appropriate position.

Thus the 2-hydroxy-6-amino derivative may be obtained from the 2-chloro-6-amino substituted xyloside by the above procedure, the chlorine atom being hydrolysed during the ring-opening step. The 6-mercapto or 2-amino-6-mercapto compound may be prepared by thiation of the corresponding 6-hydroxy substituted derivative with, for example, phosphorus pentasulphide. Subsequent alkylation with an alkyl halide, such as methyl iodide, in dimethylsulphoxide in the presence of anhydrous potassium carbonate, then produces the corresponding 6-alkylthio compounds.

The compounds of formula (II), wherein $Y^1$ is a protected mercapto group and $Y^2$ is an amino group or a hydrogen atom, provided that when $Y^1$ is a methylthio group, $Y^2$ is an amino group, are novel compounds and form a further aspect of the present invention.

The compound of formula (II) wherein $Y^1$ and $Y^2$ are both amino groups may be prepared according to the method described in the specification of co-pending British Patent Application No. 54502/70, by hydrogenation of the appropriate 2,6-diazide derivative, which is in turn prepared from the corresponding 2,6-dihalo-9-(2,3,5-tri-O-benzyl-$\beta$-arabinofuranosyl)purine. However the compounds of formula (II), wherein at least one substituent is an amino group, may preferably be obtained according to the method described and claimed in the specification of co-pending British Patent Application No. 54503/70. This method involves the acylation of the appropriately substituted purine starting material in order to protect the free amino group(s) followed by condensation with a blocked arabinose halide and finally deacylation to remove the protecting group(s). The mono-substituted 6-alkylthio compound of formula (II) may be prepared simply by condensation of the 6-alkylthio purine with the blocked arabinose halide.

Convenient acylating agents for the above method include fatty acids or derivatives having up to 6 carbon atoms, but it has been found preferable to employ a long chain acid or derivative having up to 20 carbon atoms, especially 16 or 18 carbon atoms, as described in the specification of co-pending British Patent Application No. 54503/70. At least one equivalent of acylating agent such as acetic anhydride or especially palmitoyl chloride, in a solvent such as the anhydride of the acid or pyridine, may conveniently be reacted at slightly elevated temperatures with the purine starting material.

The condensation with the arabinose halide, which has one or more of its hydroxyl groups blocked with removable blocking groups Z, as hereinbefore defined, may be carried out according to the method described by Keller et al. in *J. Org. Chem.* (1967), 32, 1944.

The preferred sugar for this purpose is 2,3,5-tri-O-benzyl-α-D-arabinofuranosyl chloride. Thus the reaction may be effected at room or elevated temperatures in a low boiling medium or solvent, preferably chloroform, in the presence of an acid trapping agent such as triethylamine.

The deacylation is carried out under basic conditions, which may be provided by suitable hydroxides or alkoxides, such as alkali metal or quaternary ammonium hydroxide. Suitable solvents for the reaction include aqueous alkanols and aqueous dimethylsulphoxide. The preferred reactants, however, are sodium hydroxide in aqueous ethanol.

In yet a further aspect the present invention provides a method for treating infections caused by DNA viruses in mammals (i.e. mice, rats, dogs, man, etc.) by administering an effective non-toxic antiviral amount of a compound of formula (I'), as hereinbefore defined, or a pharmaceutically acceptable salt thereof, to the infected animal or to an animal which may be exposed to the infection. In a particular aspect there is the method as hereinbefore defined for treating viral infections by administering a compound of formula (I) to the animal.

The following examples illustrate the invention:

EXAMPLE I 2,6-Diazido-9-(2,3,5-tri-O-benzyl-β-D-arabinofuranosyl)purine

A solution of 2.1 g. of 2,6-dichloro-9-(2,3,5-tri-O-benzyl-β-D-arabinofuranosyl)purine in 8 ml. of methanol and 2 ml. of acetone was heated with 440 mg. (2 molecular equivalents) of sodium azide for 6 hours under reflux conditions. The precipitated sodium chloride was filtered off, and the yellow filtrate, containing the 2,6-diazido-9-(2,3,5-tri-O-benzyl-β-D-arabinofuranosyl)purine showed absorption maxima at 245,270 (shoulder), 300 mμ in 95% ethanol. The filtrate was used directly for the reduction in the next step.

EXAMPLE II 2,6-Diamino-9-(2,3,5-tri-O-benzyl-β-D-arabinofuranosyl)purine

The reaction product of example I was reduced with a 5% palladium-charcoal catalyst and hydrogen at 2 atmospheres of pressure at 25°C. After 4 hours, the catalyst was removed and the filtrate was evaporated to dryness under reduced pressure. The residue (1.88 g.) was recrystallized from 95% ethanol to give 1.0 g. of pale yellow crystals, m.p. 158°–159°, which was homogeneous on thin-layer chromatography. The analysis corresponded to 2,6-diamino-9-(2,3,5-tri-O-benzyl-β-D-arabinofuranosyl)purine.

EXAMPLE III 2,6-Diamino-9-(β-D-arabinofuranosyl)purine

To 1 g. of the product of example II was added 200 ml. of liquid ammonia. Small pieces of sodium were added until the blue color persisted for several minutes. A total of 350 mg. of sodium was used. The blue color was discharged with a few crystals of ammonium chloride. The ammonia was evaporated under a stream of nitrogen and the residue was triturated with 50 ml. of benzene. The insoluble residue was taken up in a few ml. of water and neutralized with acetic acid. The product (500 mg.), after recrystallization from water, melted at 257°–259° with decomposition. The 2,6-diamino-9-(β-D-arabinofuranosyl)purine showed a λ max = 253,290 mμ at pH 1, and λ max = 257,279 mμ at pH 11.

EXAMPLE IV

2-Amino-6-hydroxy-9-(β-D-arabinofuranosyl)purine

A suspension of 10 mg/ml of an adenosine deaminase enzyme (prepared from intestinal calf mucosa) was assayed to have an activity of 210 μ moles/min. at 38°C. To a solution of 191 mg. of 2,6-diamino-9-(β-D-arabinofuranosyl)purine in 800 ml of a 1 millimole phosphate buffer of pH 7.1 was added 50 micrograms of adenosine deaminase. After two hours at 38°C. the reaction mixture was freeze dried. The resulting powder was extracted with hot methanol which was filtered and evaporated to give a solid. This solid was triturated with methanol, filtered and the methanol evaporated. The solid was dissolved in 25 ml. of warm methanol and cooled to crystallize the product, 2-amino-6-hydroxy-9-(β-D-arabinofuranosyl)purine, m.p. < 300°C.

EXAMPLE V

6-Mercapto-9-(β-D-arabinofuranosyl)purine 6-methyl-thio purine (20 g.) was condensed with 2,3,5-tri-O-benzyl-α-D-arabinofuranosyl chloride (24.2 g.) in 200 ml. CH₂Cl₂ in the presence of 4A molecular sieves and stirred for ten days at room temperature. The reaction mixture was then filtered through Celite and the methylene chloride removed in vacuo. The oil was triturated with cyclohexane, filtered and the solvent removed in vacuo to give an oil which was dissolved in absolute methanol and treated with Dowex-1-(bicarbonate) until the solution remained neutral. Filtration and evaporation of the solvent in vacuo gave crude 6-methylthio-9-(2,3,5-tri-O-benzyl-β-D-arabinofuranosyl)purine. The product was purified by chromatography on a Silica gel column with benzene-ethyl acetate. After evaporation of the solvent in vacuo the compound was obtained as a colorless oil.

Liquid ammonia (300 ml.) was distilled into a flask protected by a dry-ice condenser. A solution of 4 g. of the 6-methylthio-9,(2,3,5-tri-O-benzyl-β-D-arabinofuranosyl)purine was dissolved in absolute diethyl-ether and added to the stirred solvent (ammonia). Sodium, (1.29 g.), was added portionwise. The reaction was quenched with solid ammonium chloride. The solvent was evaporated under a stream of nitrogen and the residue was triturated with ether. The residue was dissolved in 40 ml. of H₂O and the product was purified by chromatography on a Dowex-1 (formate) column.

Elution with water followed by 0.02 N formic acid gave the product which was isolated by lyophilization. This was purified further by dissolution in aqueous ammonia, treatment with charcoal and neutralization with acetic acid to give 6-mercapto-9-($\beta$-D-arabinofuranosyl)-purine, m.p. 207°–210°C.

EXAMPLE VI

6-Methylthio-9-($\beta$-D-arabinofuranosyl)purine 6-mercapto-9-($\beta$-D-arabinofuranosyl)purine is reacted at room temperature with methyl iodide in dimethyl sulphoxide in the presence of anhydrous potassium carbonate to give 6-methylthio-9-($\beta$-D-arabinofuranosyl)purine, m.p. 99°–101°C.

EXAMPLE VII 2-amino-6-mercapto-9-($\beta$-D-arabinofuranosyl)purine

A suspension of 10 g. of 2-amino-6-methylthiopurine in 125 ml. of acetic anhydride was heated at 130° for 1.5 hours, with stirring, The reaction mixture was evaporated to one-half its volume and poured into 400 ml. of ether-pentane (1:1). The precipitate was collected, washed with ether, suspended in 90 ml. of methanol and treated with 10 ml. of concentrated ammonium hydroxide. After 30 minutes at room temperature, the mixture was cooled to 0° and filtered. The precipitate of 2-acetamido-6-methylthiopurine was washed with methanol and dried in vacuo at 60°.

A mixture of 4.46 g. of 2-acetamido-6-methylthiopurine, 4.87 g. of 2,3,5-tri-O-benzyl-$\alpha$-D-arabinofuranosylchloride, 2 g. of triethylamine and 200 ml. of acetonitrile was stirred with 4-A molecular sieves at room termperature for one week. The mixture was filtered, and the filtrate, which contained the product, was evaporated to a syrup in vacuo. The syrup was dissolved in methanol treated with Dowex-1 (bicarbonate) and the product was purified by chromatography on a Silica gel column, eluted with benzene-ethyl acetate. Evaporation of the solvent gave the syrup 2-acetamido-6-methylthio-9-(2,3,5-tri-O-benzyl-$\beta$-D-arabinofuranosyl) purine. To a solution of 1.13 g. of the compound isolated from the previous step in 20 ml. of ethanol, 0.25 ml. of 10N NaOH plus 0.5 ml. of water were added. The stirred solution was kept at 70° for 30 min. and then evaporated to dryness in vacuo. The product was extracted into ether. After evaporation of the ether, 0.92 g. of 2-amino-6-methylthio-9-( 2,3,5-tri-O-benzyl-$\beta$-D-arabinofuranosyl) purine was obtained. The identity was established by its NMR spectrum.

The 0.92 g. of the deacetylated compound was dissolved in anhydrous ether and added to 50 ml. of liquid ammonia. Sodium (0.28 g.) was then added portionwise. A few crystals of ammonium chloride were added at the end of the reaction, and the ammonia was allowed to evaporate. The residue was extracted with benzene, dissolved in water and the product was purified by chromatography on a Dowex-1 (formate) column, eluted with 0.02N formic acid. The 2-amino-6-mercapto-9-$\beta$-D-arabinofuranosylpurine (130 mg.) decomposed without melting > 300°.

EXAMPLE VIII

2-Hydroxy-6-amino-9-($\beta$-D-arabinofuranosyl)purine

A solution of 150 mg. of 2,6-diamino-9-($\beta$-D-arabinofuranosyl)-purine in 6.7 ml. of water, 0.5 ml. of 1N hydrochloric acid and 0.7 ml. of glacial acetic acid was kept at room temperature while 120 mg. of solid sodium nitrite was added in portions over a 24 hr. period. The reaction mixture was diluted with water and the resulting 2-hydroxy-6-amino-9-($\beta$-D-arabinofuranosyl)purine removed by filtration. The product was purified by dissolution in dilute sodium hydroxide, filtration, and reprecipitation by acidification to pH 6 with acetic acid. It was then washed with acetone and dried to give 70 mg. of 2-hydroxy-6-amino-9-($\beta$-D-arabinofuranosyl)purine as the monohydrate, m.p. > 300°C. (darkens ~258°C.); $\lambda$ max at pH 1 235 $\mu$, inflexion 241 m$\mu$, 282 m$\mu$, $\lambda$ max at pH 11,248 m$\mu$, 283 m$\mu$.

A small sample was hydrolyzed in hot 0.1 N hydrochloric acid. This gave 2-hydroxy-6-aminopurine as shown by thin layer chromatographic comparison with an authentic sample (solvent system - isopropanol, ammonium sulfate).

EXAMPLE IX

Pharmaceutical Preparations

In each of the following pharmaceutical preparations, the active ingredient is any one of the above compounds encompassed by formula I' but is preferably guanine-9-($\beta$-D-arabinofuranosyl)purine, i.e. 2-amino-6-hydroxy-9-($\beta$-D-arabinofuranosyl)purine or 2-amino-6-mercapto-9-($\beta$-D-arabinofuranosyl)purine.

| A. Injectable Solution | |
|---|---|
| Active ingredient | 10 mg. |
| Sodium chloride | 0.009 mg. |
| Water for injection | q.s. to 1 ml. |

The above formulation is sufficient to fill a single-dose capsule.

| B. Tablet | |
|---|---|
| Active ingredient | 10 mg. |
| Lactose | 134 mg. |
| Polyvinylpyrrolidone | 5 mg. |
| Corn starch | 50 mg. |
| Magnesium stearate | 1 mg. |

The above formulation is sufficient to comprise one 200 mg. tablet. The tablet may be enteric coated and sugar coated to prevent disintegration in the stomach.

| C. Capsule | |
|---|---|
| Active ingredient | 10 mg. |
| Lactose | 50 mg. |
| Corn starch | 138 mg. |
| Magnesium stearate | 2 mg. |

A two-piece, hard-shell, clear or opaque gelatin capsule is filled with the above formulation to a fill weight of 200 mg. The capsule may be enteric coated to prevent disintegration in the stomach.

|   D. Syrup          |              |
|---------------------|--------------|
| Active ingredient   | 10 mg.       |
| Liquid sucrose      | 3 mg.        |
| Glycerine           | 1 mg.        |
| Flavoring agent     | 0.001 mg.    |
| Distilled water     | q.s. to 5.0 ml. |

The above formulation describes a one teaspoon single dose of a syrup containing an active ingredient of this invention.

|   E. Opthalmic Solution |              |
|-------------------------|--------------|
| Active ingredient       | 1 mg.        |
| Distilled water         | q.s. to 10 ml. |

The above formulation is buffered to a pH of 6.5–7.0.

|   F. Ointment     |          |
|-------------------|----------|
| Active ingredient | 10 g.    |
| White petroleum   | 90 g.    |

EXAMPLE X 2-amino-6-methylthio-9-(β-D-arabinofuranosyl)purine

To a stirred slurry of 105 mg. of 2-amino-6-mercapto-9-(β-D-arabinofuranosyl)purine and 0.4 g. of Dowex-1-(bicarbonate) in 5 ml. of water was added 0.23 g. (0.1 ml.) of methyl iodide. After a reaction time of 2 hours at room temperature u.v. monitoring (methanol) showed no starting material remaining (disappearance of peak at 345 mμ). The resin was removed by filtration and washed with 50 ml. of methanol. The filtrate and methanol washings were evaporated at 40°C. under reduced pressure. Acetone was added and removed at 40°C. to give an off-white solid weighing 87 mg. Thin layer chromatography showed a single spot, representing 2-amino-6-methylthio-9-(β-D-arabinofuranosyl)-purine.

What we claim is:

1. A compound of formula (I) or a pharmaceutically aceptable salt thereof

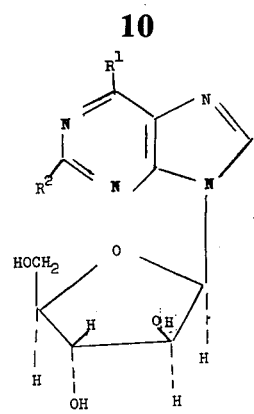

(I)

wherein $R^1$ is mercapto or lower alkylthio and $R^2$ is amino or hydrogen, or $R^1$ is amino and $R^2$ is hydroxy, provided that whenever $R^1$ is mercapto or methylthio, $R^2$ is amino, said compound having a β-configuration regarding the linkage between the purine and D-arabinofuranosyl moiety.

2. 2-Amino-6-mercapto-9-(β-D-arabinofuranosyl)-purine.

3. 2-Amino-6-methylthio-9-(β-D-arabinofuranosyl)-purine.

4. 2-Hydroxy-6-amino-9-(β-D-arabinofuranosyl)purine.

5. A compound of formula (II)

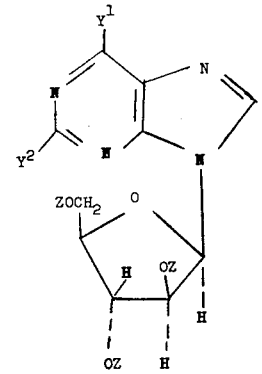

(II)

wherein $Y^1$ is protected mercapto and is protected by one of the groups consisting of lower alkyl, benzyl, p-phenylbenzyl, naphth-1-yl-methyl and naphth-2-yl-methyl and $Y^2$ is amino or hydrogen, provided that when $Y^1$ is methylthio, $Y^2$ is amino and Z is a benzyl group, said compound having a β-configuration regarding the linkage between the purine and D-arabinofuranosyl moiety.

* * * * *